United States Patent [19]

Keller et al.

[11] Patent Number: 4,623,723

[45] Date of Patent: Nov. 18, 1986

[54] PROCESS FOR SEPARATING RIBONUCLEIC ACIDS FROM A SOLUTION CONTAINING DEOXYRIBONUCLEIC ACIDS

[75] Inventors: Reinhold Keller, Bad Soden am Taunus; Merten Schlingmann, Königstein, both of Fed. Rep. of Germany

[73] Assignee: Hoechst Aktiengesellschaft, Frankfurt, Fed. Rep. of Germany

[21] Appl. No.: 588,068

[22] Filed: Mar. 9, 1984

[30] Foreign Application Priority Data

Mar. 12, 1983 [DE]  Fed. Rep. of Germany ....... 3308932

[51] Int. Cl.$^4$ ..................... C07H 15/12; C07H 17/00
[52] U.S. Cl. ........................................ 536/27; 536/28; 536/29
[58] Field of Search ............................. 536/27, 28, 29

[56] References Cited

U.S. PATENT DOCUMENTS 4,206,243  6/1980  Schlingmann et al. ............. 426/429
4,482,482 11/1984  Haff et al. ............................. 536/29

FOREIGN PATENT DOCUMENTS 2027033  2/1980  United Kingdom .

OTHER PUBLICATIONS

Ahonen et al., Separation of tRNA from DNA by Gel Filtration, Chem. Abstracts 65: 20411g (1966).
Ikeguchi, Membrane Separation, Chem. Abstracts 88: 107401a (1977).
Freifelder, Physical Biochemistry, pp. 143 and 220-221 (1976).
Hombach, Molecular Size Distributions of Coal Derivatives, Chem. Abstracts 96: 125956e (1982).
Toyomoto, Hollow Fiber-Type Ultrafiltration Systems, Chem. Abstracts 88: 172457n (1977).
Breslau et al., Advances in Hollow Fiber Ultrafiltration Technology, Chem. Abstracts 94: 141725t (1980).
Berns et al., Isolation of High Molecular Weight DNA from Haemophilus Influenzae, Chem. Abstracts 63: 2033c (1965).
Staude, Current Status of Separation Technology with Membranes, Chem. Abstracts 91: 22958z (1979).

*Primary Examiner*—Ethel G. Love
*Attorney, Agent, or Firm*—Finnegan, Henderson, Farabow, Garrett & Dunner

[57] ABSTRACT

Crude nucleic acid solutions can be selectively separated using a membrane separating process, it being possible for the high molecular weight DNA to be isolated from the retentate and the low molecular weight RNA to be isolated from the permeate. Ultrafiltration on hollow fiber membranes is preferred.

6 Claims, No Drawings

PROCESS FOR SEPARATING RIBONUCLEIC ACIDS FROM A SOLUTION CONTAINING DEOXYRIBONUCLEIC ACIDS

When obtaining protein for human nutrition from agglomerates of microbial cells, it is necessary largely to remove the nucleic acids. This is advantageously carried out by the process described in German Patent Specification No. 2,633,666 (U.S. Pat. No. 4,206,243), in which initially the lipids are removed with an extraction mixture comprising a polar solvent, preferably methanol, and ammonia, whereupon the nucleic acids are extracted with water. These crude nucleic acid extracts contain, in addition to ribonucleic acids, RNA in the following text, deoxyribonucleic acids, DNA in the following text.

5'-Ribonucleotides are used as starting materials for the preparation of foodstuffs additives and for medicaments. Their preparation by enzymatic hydrolysis of RNA has been disclosed. However, the enzyme used for this purpose, 5'-phosphodiesterase, not only hydrolyzes RNA, but also, at the same time, DNA, so that in addition to the desired 5'-ribonucleotides, 5'-deoxyribonucleotides are also produced as by-products. These by-products can be separated from the 5'-ribonucleotides only with great difficulty. For this reason, processes for the preparation of pure RNA have already been disclosed. These include the selective precipitation of RNA by heating and subsequent acid treatment, as is described in Japanese Patent Application No. 78-20,493. In the process in Japanese Patent Application No. 79-55,791, the acid precipitation of RNA takes place in the presence of divalent cations. Thus, in this process, the DNA is decomposed by a heat and acid treatment. Moreover, a considerable proportion of the RNA is also lost in this process.

A process for the preparation of 5'-ribonucleotides has already been proposed, which process comprises selectively hydrolyzing a solution of crude nucleic acids, which contains RNA, with a 5'-phosphodiesterase immobilized on a polymeric support, and isolating the unchanged DNA and the 5'-ribonucleotides from the hydrolysate by known processes of purification and separation (German Offenlegungsschrift No. 3,136,940).

It has now been found that the RNA in crude nucleic acid solutions can be separated from the DNA by subjecting this solution to a membrane separating process. In this process, use is made of the difference in molecular weight between the relatively high molecular weight DNA and the relatively low molecular weight RNA. The exclusion limit of the membrane is selected to accord with the known or determined molecular weights of the nucleic acids to be separated.

Membrane separating processes are generally familiar and especially so in biotechnology (review article: H. Strathmann, Chemie-Technik 11 (1982) 813–819). Ultrafiltration in plate, tube, capillary tube, wrapped membrane and, in particular, hollow fiber equipment is preferred for the process according to the invention.

The preferred starting materials used are crude nucleic acids from bacteria, in which the ratio of RNA to DNA is usually about 4:1. It is important to employ crude nucleic acid solutions in which the DNA has been degraded either not at all or only inconsiderably, that is to say starting solutions in which the natural difference in molecular weight between DNA and RNA has largely been retained. The process disclosed in German Patent Specification No. 2,633,666 is also advantageous in this respect.

The permeates obtained according to the invention can be degraded in a known manner, for example enzymatically, to give the 5'-ribonucleotides. The retentates can be further processed in the same manner to give the 5'-deoxyribonucleotides which have a wide variety of uses, for example in genetic engineering. The invention is illustrated in more detail in the following examples.

EXAMPLE 1

A bacterial agglomerate obtained in accordance with U.S. Pat. No. 4,166,004, Example 2, and having a nucleic acid content of 11.2% by weight and a residual moisture content of 2 to 4% by weight was treated in a fluidized bed at an air temperature of 160° C. for 30 minutes, a product temperature of 120° C. being maintained for 10 minutes. Then, in accordance with Example 1 in U.S. Pat. No. 4,206,243, this heat-treated cell agglomerate was extracted with methanolic ammonia, washed with methanol and dried in vacuo at 40° C. for 5 hours.

The dry cell agglomerate was suspended in 10 times the amount by weight of water and homogenized by stirring. After raising the temperature to 55° C., stirring was continued for a further 20 minutes, then the suspension was cooled to 30° C. and separated into a solid and a liquid phase by centrifugation. The resulting sediment was again mixed with the same amount of water and stirred at 20° C. for 10 minutes. Then centrifugation was repeated and the liquid phases were combined. They contain 9 g of nucleic acids per liter with a RNA/DNA ratio of 4:1.

100 liters of this crude nucleic acid solution are clarified by filtration through a deep filter medium and the filtrate is passed into a hollow fiber ultrafiltration device (Amicon DC 50 EM, hollow fiber cartridge, molecular weight separating limit 100,000). This concentrates the crude nucleic acid solution to 10 liters and it is then subjected to diafiltration with 10 liters of deionized water.

The retentate thus obtained contains the DNA with contamination by less than 1% of RNA, and the permeate contains the RNA without contamination by DNA.

In order to isolate the DNA and RNA, the retentate and the permeate respectively are cooled to 5° C. and the pH of the solution is adjusted to 2.0 with hydrochloric acid. The precipitated DNA and RNA are removed by centrifugation and dried.

EXAMPLE 2

The starting crude nucleic acid solution was obtained in accordance with Example 8 in U.S. Pat. No. 4,206,243, but the nucleic acids therein were only extracted with water. This crude nucleic acid solution is concentrated to a content of 30 g of nucleic acids per liter. The RNA/DNA ratio was 3:1.

50 liters of this crude nucleic acid solution were initially filtered and then subjected to ultrafiltration as described in Example 1. The retentate concentrated to 5 liters was dialyzed with 5 liters of deionized water. The DNA was precipitated from the retentate thus washed after cooling down to 5° C. and adjusting the pH to 2.0, and was isolated. The RNA is obtained from the permeate analogously.

We claim:

1. A process for separating deoxyribonucleic acid from ribonucleic acid in crude nucleic acid solutions, in which the natural difference in molecular weight between deoxyribonucleic acid and ribonucleic acid has been largely retained, which comprises subjecting the crude nucleic acid solution to an ultra-filtration process, the deoxyribonucleic acid being held back and the ribonucleic acid permeating through.

2. The process as claimed in claim 1, wherein a membrane with a molecular weight separating limit of 100,000 is employed.

3. A process as claimed in claim 1, wherein the ultra-filtration process is a hollow fiber process.

4. The process as claimed in claim 1, wherein the crude nucleic acid solution is of bacterial origin.

5. The process as claimed in claim 1, wherein the crude nucleic acid solution is obtained by extracting a bacterial cell agglomerate at first with an extraction mixture consisting of ammonia and a lower alcohol, which mixture contains at most 30% of water, referred to the weight of said alcohol, and thereafter with water in an essentially neutral pH-range, which aqueous extract is the crude nucleic acid solution.

6. A process as claimed in claim 5, wherein the lower alcohol is methanol.

* * * * *